United States Patent [19]

Greenstein et al.

[11] Patent Number: 4,945,897
[45] Date of Patent: Aug. 7, 1990

[54] SURGICAL RETRACTOR

[75] Inventors: Robert Greenstein, Tenafly, N.J.; Nash Aussenberg, New York, N.Y.

[73] Assignee: Automated Medical Products Corp., New York, N.Y.

[21] Appl. No.: 355,439

[22] Filed: May 22, 1989

[51] Int. Cl.5 ............................................. A61B 17/02
[52] U.S. Cl. ..................................................... 128/20
[58] Field of Search ...................... 128/20, 17, 18, 345; 606/191

[56] References Cited

U.S. PATENT DOCUMENTS

| | | | |
|---|---|---|---|
| 1,963,173 | 6/1934 | Morin | 128/20 |
| 2,863,444 | 12/1958 | Winsten | 128/20 |
| 3,463,144 | 8/1969 | Hammond | 128/20 |
| 3,522,800 | 8/1970 | Lesser | 128/20 |

OTHER PUBLICATIONS

Mueller, "The Surgical Armamentarium", 1980 pp. 65, 346, 478, 697.

Primary Examiner—Edward M. Coven
Assistant Examiner—Mark S. Graham
Attorney, Agent, or Firm—Neuman, Williams, Anderson & Olson

[57] ABSTRACT

A retractor is provided for use in performing a surgical procedure such as correcting the morbid obesity of a patient. The retractor incorporates a blade section and a handle section protruding from a first peripheral segment of the blade section. The blade section includes a first portion connected to the handle section and an elongate second portion extending angularly from the first portion. The second portion is provided with an elongate open end slot extending from a distal end of the second portion and terminating in the vicinity of a juncture between the first and second portions. The slot forms the blade section second portion into a pair of finger-elements. Each element has a first surface which is adapted to engage a perimetrical segment of an incision made in the patient during the surgical procedure.

10 Claims, 1 Drawing Sheet

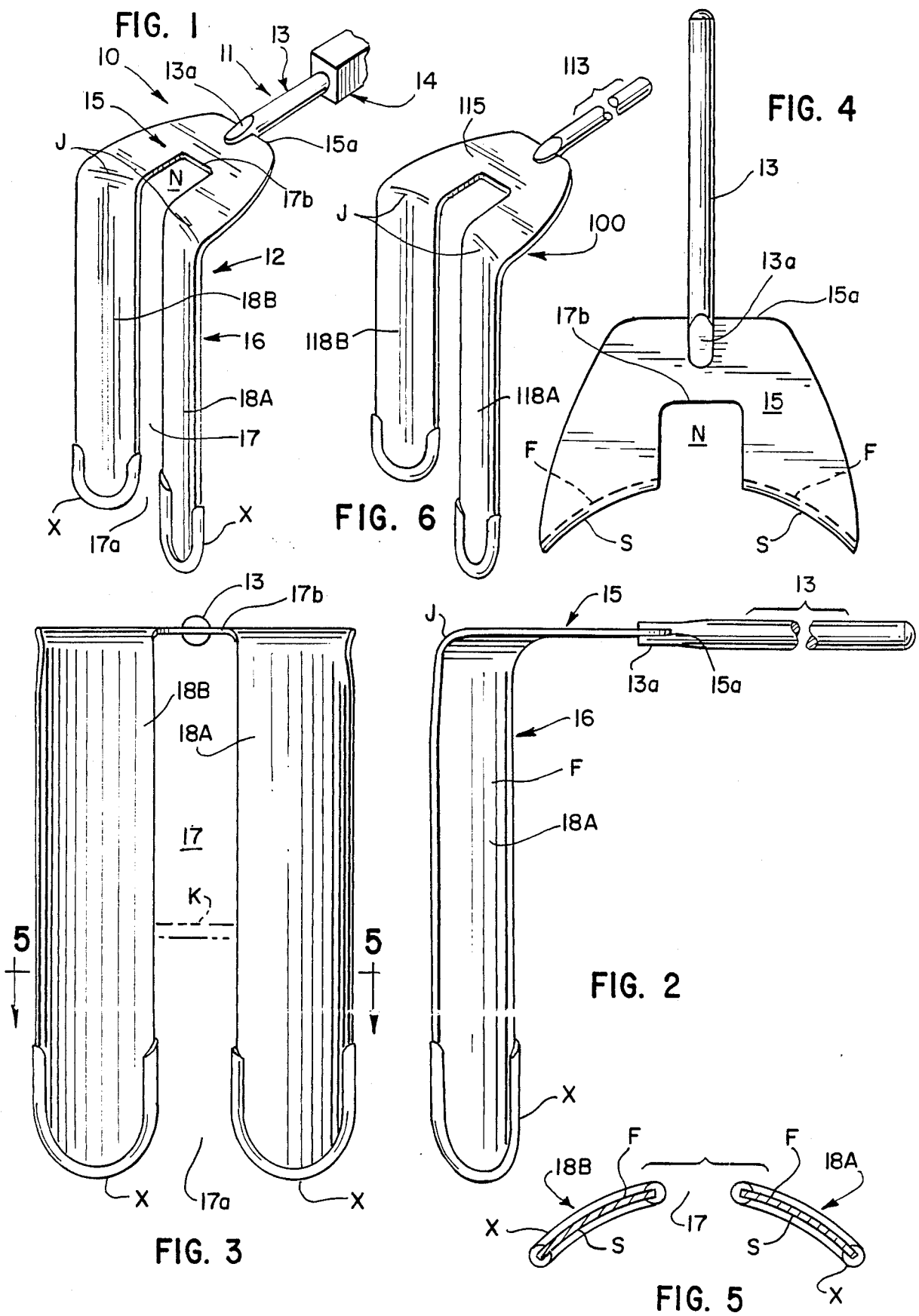

SURGICAL RETRACTOR

BACKGROUND OF THE INVENTION

In performing certain surgical procedures for the morbidly obese, and esophagectomy, rectal and gallbladder, the use of various types of retractors is a common practice. In many such procedures, however, the configuration of certain of the prior retractors created a problem for the surgeon by obstructing the normal positioning and manipulation of certain surgical instruments and for the patient because such retractors caused parts of the patient's body to become destended, distorted or bruised resulting in post-operative pain or discomfort. Furthermore, prior retractors were oftentimes awkward to manipulate and required an inordinate amount of dexterity to assemble and disassemble and to adjust so as to accommodate a particular anatomical condition.

SUMMARY OF THE INVENTION

Thus, the improved surgical retractor readily overcomes the aforenoted shortcomings of the prior art.

The improved surgical retractor is of simple, yet sturdy, construction and may be readily cleaned and sterilized for reuse.

Further and additional virtues possessed by the improved retractor will become apparent from the description, accompanying drawing and appended claims.

In accordance with one embodiment of the invention, a retractor is provided for use in performing a surgical procedure. The retractor includes a handle section allowing the retractor to be readily assembled on, disassembled from and adjusted relative to a conventional holder or clamp. A blade section extends from the handle section and includes a first portion to which the handle section is attached and an elongate second portion which is integral with and extends angularly from the first portion. The second portion is provided with a pair of elongate finger-like elements which are separated from one another by a longitudinally extending, open end slot. One end of the slot terminates in the vicinity of a juncture between the first and second portions. The finger-like elements are adapted to engage a perimetric segment of the patient's incision. The distal ends of the finger-like elements are blunt and beaded to minimize trauma to organs and connective tissue.

DESCRIPTION

For a more complete understanding of the invention, reference is made to the drawings wherein:

FIG. 1 is a fragmentary, perspective view of one embodiment of the improved retractor shown attached to a conventional holding device.

FIG. 2 is an enlarged, fragmentary, side elevational view of the retractor of FIG. 1.

FIG. 3 is a front elevational view of the retractor of FIG. 2 and showing in phantom lines a bridge piece interconnecting corresponding segments of the finger-like elements of the retractor.

FIG. 4 is a fragmentary top plan view of the retractor of FIG. 2.

FIG. 5 is an enlarged sectional view of the retractor taken along line 5—5 of FIG. 3.

FIG. 6 is a fragmentary perspective view of a second embodiment of the improved retractor. Referring now to the drawings, an improved retractor 10 is shown which is particularly suitable for use in performing procedures (e.g. gastroplasty procedure) involving morbidly obese, esophagectomy, rectal and gallbladder surgery. The retractor is of unitary construction and is formed preferably of high grade steel and includes a handle section 11 and a blade section 12. The handle section 11 in the illustrated embodiment is formed of a rod section 13 which is sized to adjustably fit within a suitable holding device 14, the latter normally being connected to a portion of the operating table, not shown, supporting the patient. The length of the rod section 13 may vary, but should be sufficient to allow the surgeon or assistant to readily manipulate the retractor between operative and inoperative modes without the retractor becoming disengaged from the holding device 14.

The blade section 12 includes an upper, or first, portion 15 which preferably has a planar, or flat, configuration. One end 13a of the handle rod section 13 is fixedly attached to a peripheral segment 15a of the first portion 15.

The blade section 12 also includes an elongate second portion 16 which is integral with and extends angular (e.g. 90°) from a peripheral segment of the first portion which is opposite segment 15a and forms a juncture J between the two portions. Formed within the second portion 16 and extending longitudinally thereof is a centrally disposed slot 17 which is open at one end 17a and terminates at the lower, or distal, end of the second portion 16. The opposite end 17b of the slot preferably terminates within the first portion 15, as shown, or in some instances at or below the juncture J. The location of the slot closed end 17b will depend in large measure on the type of surgery being performed. In the illustrated embodiment the slot closed end forms a notch N which extends from the juncture J towards the handle section 11.

In surgery, where a conventional surgical staple gun, not shown, is utilized to produce a vertical staple line on the patient, the notch N will readily accommodate an elongate section of the gun thereby allowing the surgeon to more accurately position the discharge head of the gun within the exposed interior of the patient's incision. Thus, by facilitating positioning of the gun discharge head within the patient's incision, the trauma normally experienced by the patient is significantly reduced because certain organs (e.g. xiphoid) or areas proximate thereto, within the patient and adjacent the area of the incision are not subjected to an inordinate amount of distension or distortion. Furthermore, because the notch facilitate the manipulation and location of certain instruments, the surgery is expedited with resulting benefit to both the patient and surgeon. The notch N also enables the surgeon and assistants to more readily observe certain areas proximate the incision.

By reason of the centrally disposed slot 17 the second portion 16 comprises a pair of elongate depending, substantially parallel finger-like elements or limbs 18A, 18B. In the form of the retractor 10, shown in FIG. 1, the finger-like elements 18A, 18B have the same longitudinal dimension. In the modified retractor 100, shown in FIG. 6, one of the finger-like elements (e.g. 118A) has a greater longitudinal dimension than the other. In certain types of surgery the modified retractor is preferred.

In either embodiment, the distal, or lower, ends 18AA, 18BB or 118AA, 118BB of the elements are blunt. The bluntness may be effected by rounding the distal end and then forming a peripheral bead X which encompasses the rounded end edge. The bead X adds thickness to the distal end and thus, eliminates the possibility of the distal ends accidentally or inadvertently tearing, cutting or puncturing interior portions of the patient when the retractor is being positioned within the incision and manipulated to an operative mode.

As noted in FIGS. 1, 2 and 4, each finger-like element has an elongate first surface F having a curved or convex configuration. Surface F is adapted to engage a tissue portion of the patient circumjacent the incision. The opposite, or second surface S of each finger-like element may have a concave configuration. The convex-concave configuration of each finger-like element enhances the strength thereof without increasing the gauge of the material from which the retractor is made.

As seen in FIG. 4, the concave and/or the convex surfaces of the pair of finger-like elements 18A–B and 118A–B preferably have a common center of curvature, not shown.

In instances where the finger-like elements have a substantial longitudinal dimension (e.g. greater than 8") in order to accommodate an incision of comparable depth, a bridge piece K, shown in phantom lines in FIG. 3 may be incorporated in the retractor in order to restrain distortion of the finger-like elements when the retractor is being manipulated to an operative mode. The bridge piece K is positioned within the slot 17 and spaced from the distal ends of the elements 18A, 18B a predetermined amount (e.g. 2 ½"–3"). The piece K spans the width of the slot and has the opposite ends thereof affixed to the corresponding elements.

In some instances, where a separate light source of high intensity, not shown, is utilized and must be positioned within, or in close proximity to, the incision, the first portion 15 of the retractor blade section 12 may be provided with, or have clamped thereto, a bracket for such light source. The inclusion of such a bracket on the retractor is an optional feature.

The improved retractors 10 and 100 are a particularly suitable for use in performing gastroplasty surgery for morbid obesity in a safer, facile and expeditious manner and with significantly reduced patient trauma. In such surgery a vertical staple line has to be created on the abdomen of the patient. Thus, the notch N, aforedescribed, which is formed in the blade section of the retractor, permits a portion of the surgical staple gun to be accommodated therein. This increased cephlad access decreases bunching of gastric tissue at the upper end of the staple line. By the staple gun fitting through the notch N, it is easier to get the angle of His completely included in the staple line, thereby forming a complete partition between pouch and stomach of the patient. In addition, the notch N also accommodates the patient's protruding xiphoid, which is attached to the sternum, and thus, effectively prevents crushing or distorting thereof which would produce undesirable post-surgery trauma for the patient. Retractor 10 is also very useful in performing surgical procedures including cholecystectomy, common bile duct exploration and in dissecting the esophagus.

Where the retractor 100 is used in place of retractor 10, in performing surgical therapy for morbid obesity, the shorter finger-like element or limb 118B allows the surgeon's finger to circumvent the patient's stomach by placing the finger behind the stomach and below the left gastric artery. The finger is then brought out at the angle of His, whereby, the gastro-hepatic omentum located above the patient's left gastric artery need not be divided or mobilized. Thus, the shorter element 118B minimizes trauma to the gastro-hepatic omentum.

The longer finger-like element 119A, on the other hand, has a specific function; namely, to expose the angle of His to the left of the esophagus, while insinuating itself between the esophagus and the spleen of the patient. The spleen is a very friable organ located in the region of the abdomen where dissection is being performed and may be easily damaged during the circumvention maneuver of the stomach. Thus, the longer finger-like element 118A provides protection for the spleen.

Additional surgical procedures may be significantly benefitted by the use of the improved retractors. Thus, the size and shape of the improved retractor may vary from that illustrated herein and will depend upon the requirements of the particular surgical procedure being performed and the physical dimensions and condition of the patient.

Thus, an improved retractor has been disclosed which is of simple, yet sturdy, construction; is easily manipulated by he surgeon or assistant during the surgical procedure; and may be beneficially and safely used in performing a variety of surgical procedures with a reduction in a patient's post-operative trauma.

We claim:

1. A surgical retractor for use with an adjustable holder in performing a gastroplasty procedure for morbid obesity wherein such procedure requires a vertical line to be formed on the abdomen of a patient by the head of a surgical staple gun, said retractor being of unitary construction and comprising a blade section having an exposed upper first portion and an elongate substantially transverse second portion depending from a juncture formed between said first and second portions for disposition within an incision made in the patient; and a handle section disposed opposite the juncture and extending laterally from a peripheral segment of said first portion; said blade section second portion including a pair of substantially rigid finger-like elements, each element having a substantially broad convex exterior first surface for engaging a tissue portion of the patient circumjacent the incision, said blade section including an elongate slot disposed intermediate said finger-like elements; said slot having a depending first segment extending the full length of said finger-like elements and having an open lower end, and a second segment extending transversely of said first segment and terminating within the blade section upper first portion at a substantial distance from the juncture of said first and second portions, said second segment forming a notch within the blade section upper first portion, said notch being adapted to accommodate the head of the surgical staple gun during the gastroplasty procedure; the lower end portion of each depending finger-like element having a blunt configuration.

2. The retractor of claim 1 wherein the blunt lower end portion of each element has an increased material thickness.

3. The retractor of claim 1 wherein at least one of the elongate finger-like elements is provided with a substantially concave exterior second surface opposite said first surface.

4. The retractor of claim 1 wherein the finger-like elements are of substantially like configuration.

5. The retractor of claim 1 wherein the elongate slot has a longitudinal axis substantially aligned with the protruding handle section.

6. The retractor of claim 1 wherein the elongate finger-like elements have substantially equal longitudinal dimensions.

7. The retractor of claim 1 wherein one elongate finger-like element has a longer longitudinal dimension than the other element.

8. The retractor of claim 3 wherein both elements are provided with a substantially concave exterior second surface the concave surfaces of the pair of finger-like elements have a substantially common center of curvature.

9. The retractor of claim 1 wherein the first portion of the blade section has a substantially planar configuration.

10. The retractor of claim 1 wherein the second portion of the blade section includes a bridge means disposed within the slot and extending transversely of and interconnecting corresponding segments of said finger-like elements; said bridge means being disposed a predetermined longitudinal distance from the slot open end.

* * * * *

UNITED STATES PATENT AND TRADEMARK OFFICE
CERTIFICATE OF CORRECTION

PATENT NO. : 4,945,897

DATED : August 7, 1990

INVENTOR(S) : Robert Greenstein, et al

It is certified that error appears in the above-identified patent and that said Letters Patent is hereby corrected as shown below:

Col. 3, line 39, delete "a"

Col. 5, last line, after "surface" insert --;-- before "concave" insert --convex and --

Signed and Sealed this

Tenth Day of September, 1991

Attest:

HARRY F. MANBECK, JR.

Attesting Officer

Commissioner of Patents and Trademarks